(12) United States Patent
Mazzoleni

(10) Patent No.: US 9,921,143 B2
(45) Date of Patent: Mar. 20, 2018

(54) PORTABLE BRINELL TESTING APPARATUS

(71) Applicant: Giancarlo Mazzoleni, Philadelphia, PA (US)

(72) Inventor: Giancarlo Mazzoleni, Philadelphia, PA (US)

( * ) Notice: Subject to any disclaimer, the term of this patent is extended or adjusted under 35 U.S.C. 154(b) by 156 days.

(21) Appl. No.: 15/046,636

(22) Filed: Feb. 18, 2016

(65) Prior Publication Data

US 2016/0245735 A1    Aug. 25, 2016

Related U.S. Application Data

(60) Provisional application No. 62/118,484, filed on Feb. 20, 2015.

(51) Int. Cl.
*G01N 3/42* (2006.01)

(52) U.S. Cl.
CPC ....... *G01N 3/42* (2013.01); *G01N 2203/0098* (2013.01)

(58) Field of Classification Search
CPC .................. G01N 3/42; G01N 2203/0098
USPC ............................................. 73/81
See application file for complete search history.

(56) References Cited

U.S. PATENT DOCUMENTS

| | | | | |
|---|---|---|---|---|
| 1,646,195 A * | 10/1927 | German | ............. | G01N 3/42 73/81 |
| 2,088,371 A * | 7/1937 | Gogan | ............. | G01N 3/44 188/314 |
| 2,188,992 A * | 2/1940 | Wolpert | ............. | G01N 3/42 353/78 |
| 2,418,916 A * | 4/1947 | Weaver | ............. | G01N 3/42 73/81 |
| 3,309,916 A * | 3/1967 | Pearson | ............. | G01N 3/42 73/81 |
| 3,421,364 A * | 1/1969 | Moneypenny | ............. | G01N 3/48 73/82 |
| 3,581,774 A * | 6/1971 | Oeland, Jr. | ............. | F15B 1/04 138/31 |
| 4,245,496 A * | 1/1981 | Napetschnig | ............. | G01N 3/44 73/83 |
| 4,691,559 A * | 9/1987 | Fischer | ............. | G01N 3/42 73/81 |
| 4,899,577 A * | 2/1990 | Fischer | ............. | G01N 3/42 73/82 |
| 5,937,721 A * | 8/1999 | Albright | ............. | B26D 7/2635 83/498 |
| 6,247,356 B1 * | 6/2001 | Merck, Jr. | ............. | G01N 3/42 73/82 |
| 7,454,960 B2 * | 11/2008 | Ernst | ............. | G01N 3/42 73/78 |
| 8,087,282 B2 * | 1/2012 | Sawa | ............. | G01N 3/42 73/1.89 |
| 8,590,367 B2 * | 11/2013 | Biddle | ............. | G01N 3/42 137/539.5 |

(Continued)

*Primary Examiner* — Lisa Caputo
*Assistant Examiner* — Nathaniel T Woodward
(74) *Attorney, Agent, or Firm* — William B. Ritchie

(57) ABSTRACT

A portable Brinell testing apparatus that meets the load time requirements of the ASTM E10 standard. The invention uses a constant force spring connected to a lever arm which is pivoted on fulcrum 32. The mechanical advantage of the mechanism is able to achieve a force of up to 3000 Kgf with constant force spring 26 that can be activated by the operator.

3 Claims, 2 Drawing Sheets

(56) References Cited

U.S. PATENT DOCUMENTS

| | | | | |
|---|---|---|---|---|
| 2004/0134263 A1* | 7/2004 | Tsujii | ............... | G01N 3/42 73/81 |
| 2014/0224003 A1* | 8/2014 | Zhang | ............... | G01N 3/42 73/82 |
| 2015/0362416 A1* | 12/2015 | Biddle | ............... | G01N 3/42 73/82 |

* cited by examiner

PORTABLE BRINELL TESTING APPARATUS

This application claims benefit of U.S. Provisional Application Ser. No. 62/118,484, filed Feb. 20, 2015, pursuant to 35 USC § 119(e).

FIELD OF THE INVENTION

This invention relates to hardness testing equipment, in particular, portable testing equipment for a Brinell test meeting ASTM E10 standard.

BACKGROUND OF THE INVENTION

The Brinell scale characterizes the indentation hardness of materials through a scale of penetration of an indenter, loaded on a material test-piece. According to the American Society of Testing and Materials (ASTM) E10 Standard, the Brinell test requires the application to an indenter of 10 mm in diameter of a determined test force (load), usually 500 Kgf for Aluminum and 3000 Kgf for Steel for a specified amount of time, with a minimum of 10 seconds and a maximum of 30 seconds.

Current portable Brinell Testers as disclosed in U.S. Patent Application Publication No. 2014/0230529, published Aug. 21, 2014, which is based on its predecessor, U.S. Pat. No. 3,129,582, employs a hydraulic cylinder activated by a hand pump with a release valve when a certain pressure therefore a certain resulting load is achieved. The problem with this approach is that the load is only applied instantaneously and it does not remain applied for the specified time; therefore, the test does not meet the ASTM E10 specification but an ad-hoc specification, E110 created just for this instrument. Some users can test according to this specification but the majority must meet the full E10 specification.

Thus, there is not found in the prior art a portable Brinell testing apparatus that meets the ASTM E10 standard.

SUMMARY OF THE INVENTION

It is an aspect of the invention to provide a portable Brinell testing apparatus that meets ASTM E10 standard.

It is still another aspect of the invention to provide a portable Brinell testing apparatus that can be made costing substantively the same as prior art portable Brinell testing apparatus.

DETAILED DESCRIPTION OF THE INVENTION

Figure 1:
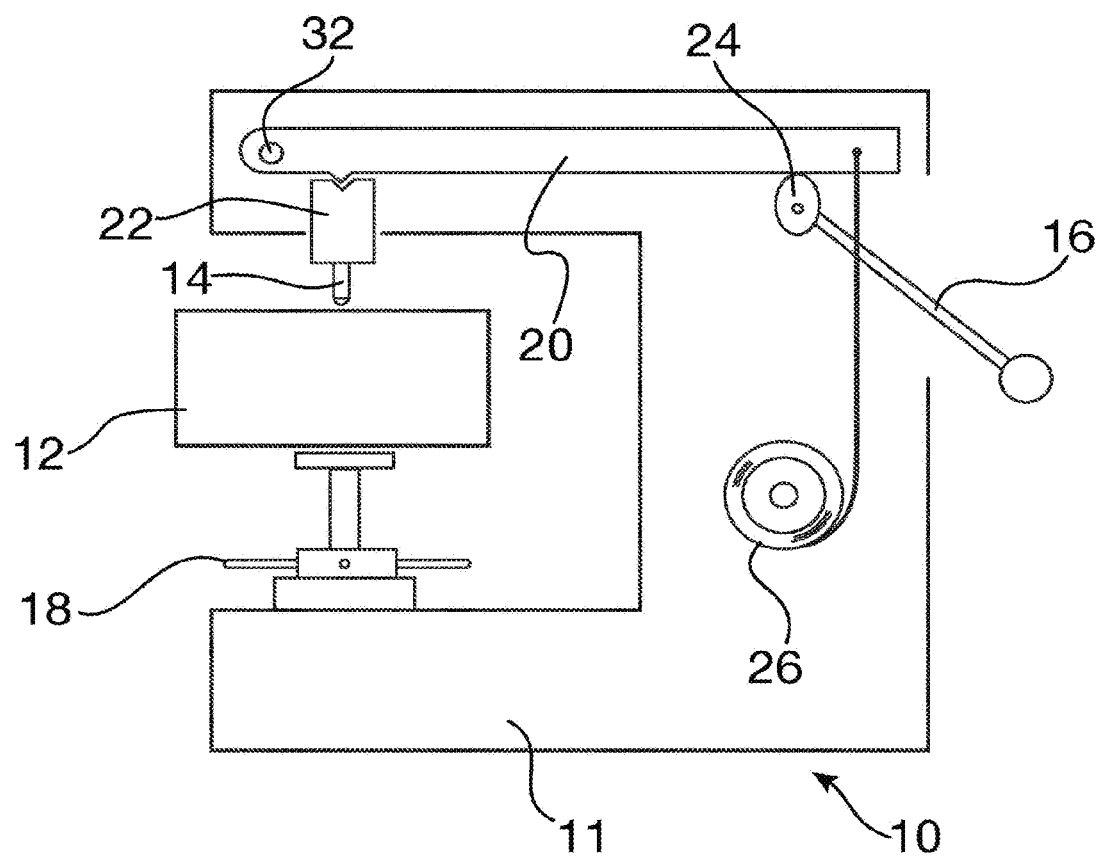
FIG. 1 is a schematic of the portable Brinell hardness testing apparatus in accordance with the invention.

As shown in FIG. 1, portable instrument 10 in accordance with the invention is shown. The problem is solved by using constant force spring 26 connected to lever arm 20 which is pivoted on fulcrum 32. The mechanical advantage of the mechanism is able to achieve a force of up to 3000 kg with constant force spring 26 that can be activated manually by the operator.

Using just regular coil springs released onto the indenter does not work because as the force is applied, indenter 10 travels into the material causing the springs to extend; therefore, lowering the load applied. The solution represented here uses constant force spring 26, which as the name implies, maintains the same force (load) as spring 26 is extended or retracted. A constant force spring 26 (such as made by Hunter Spring Products Company of Feasterville, Pa., Model Negator Spring SH31U58) would be suitable.

Constant force spring 26 in invention 10 is selected to minimize the small variation that still exists in constant force springs. This is achieved by specifying a long nominal travel of the spring, but using only a small part of such travel and in the area of extension where the line force/displacement is most flat; that is, mostly constant force. Multiple springs can be combined on a single drum to achieve the high load required.

In operation, invention 10 works as follow:

Test piece 12 is placed onto tester 10 specifically on elevating screw assembly 18 which is a jack screw well known in the art. Test piece 12 is raised until test piece 12 contacts indenter 14 and closes the gap between indenter holder 22 and loading beam 20.

At this point, the load is applied by lever 16 connected to eccentric cam 24 that allows constant force spring 26 to pull lever arm 20 having fulcrum 32.

Each pivot point is fitted with bearings, again, well known in the art. Loading beam 20 with fulcrum 32, thus, applies the load to indenter holder 22 and indenter 14. Constant force spring 26 retracts as indenter 14 travels into test piece 12 but the flat force/displacement characteristic of spring 26 assures that the load on indenter 14 remains constant.

The specified time for applying the force is typically a minimum of 10 sec. as measured by a stopwatch. Cam 24 is rotated back to the resting position which removes the test load. Then, by lowering elevating screw assembly 18, the test piece can be removed.

The force can be calibrated by moving the contact point on lever forward/back. This calibration only has to be done the first time at the time of manufacture. Verification or re-calibration is necessary only periodically, such as every 12 months or so.

The addition of a button load cell (such as made by Forsentek of Shenzhen, China, Model No. FC50 (5000 Kg capacity)) in combination with a sensor Load Cell Amplifier Model LAU 63.1 (such as made by Sensor Techniques of Cowbridge, UK) connected to a readout display (such as provided by SENECA DISPLAY of Padova, Italy, Model S311AK) and powered by a battery pack, (such as model no. CU-J970 made by AA PORTABLE POWER PAC of Richmond, Calif.), a user can then read the actual load being applied.

While this invention has been described for use with a portable system, the invention could also be used with a bench Brinell tester that is firmly fixed in a location.

Figure 2:
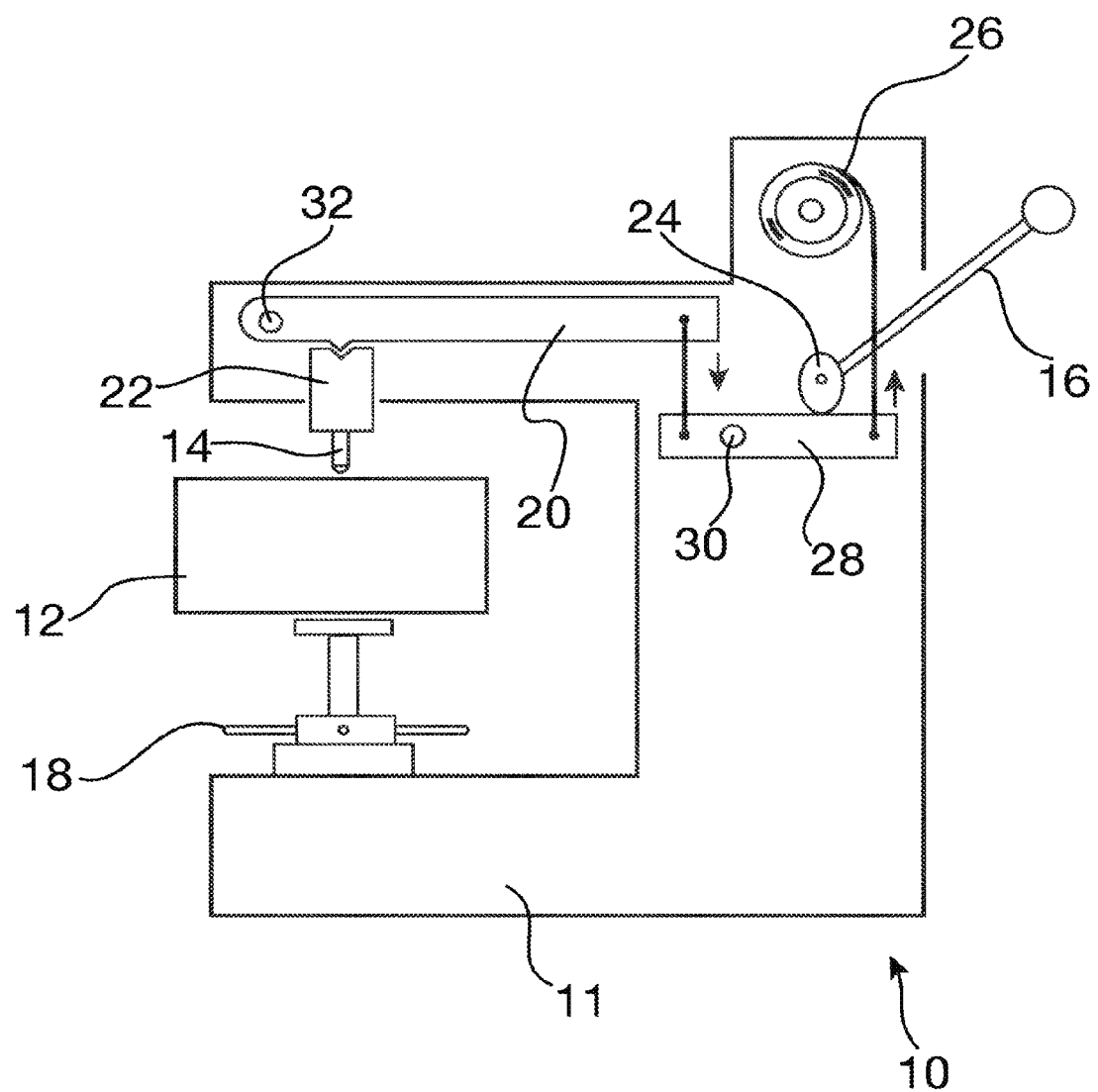
FIG. 2 is a schematic of an alternative embodiment of the portable Brinell hardness testing apparatus.

As shown in FIG. 2, an alternative embodiment is provided. More than one lever is used to gain mechanical advantage. While two lever arms are shown, more than two could also be used. In this case, there is an addition of secondary beam 28 with fulcrum 30. This beam 28 is connected to beam 20 via arm 34.

In this embodiment, two advantage levers 28, 20 wherein levers 28 and 20 are pivotally connected to one another via arm 34. Manual lever 16 is used to apply the force with constant force spring 26 placed above secondary lever arm 28. In this case, lever arm 16 causes cam 24 to raise secondary lever arm 28, pivoting around fulcrum 30 which, in turn, pulls down lever arm 20 via fulcrum 30, thus, by pivoting beam 20 on fulcrum bearing 32. Constant force spring 26 causes a constant force to be applied to indenter 14 even as indenter 14 moves into test piece 14.

This embodiment can also be fitted with a timer, button load cell, readout display and battery pack described above.

Although the present invention has been described with reference to certain preferred embodiments thereof, other versions are readily apparent to those of ordinary skill in the preferred embodiments contained herein.

What is claimed is:

1. A Brinell testing apparatus for measuring the hardness of a test material positioned in said apparatus between an indenter in a holder and an elevated screw assembly such that said apparatus comprises:
 a lever arm in communication with the indenter in the holder wherein said lever arm has a fulcrum at one end and wherein said lever arm has an eccentric cam at the other end wherein said fulcrum is in contact with one end of the lever arm while the eccentric cam is in contact with the other end such that the mechanical advantage of said lever arm is able to achieve a force of up to 3000 Kgf by rotating said eccentric cam; and
 a constant force spring is attached to the other end of said lever arm adjacent to said eccentric cam such that force being applied to the indenter remains constant despite the movement of the indenter into the test material during the required time period of the test.

2. The Brinell testing apparatus of claim 1 further comprising a handle attached to said cam wherein a user pulling on said handle causes said cam to rotate thereby causing the force to be exerted on the indenter.

3. The Brinell testing apparatus of claim 1 wherein said lever arm comprises a plurality of levers such that the mechanical advantage of said plurality of levers is greater than the mechanical advantage of a single lever arm.

* * * * *